July 1, 1969 F. MILLS Plant Pat. 2,899

PIN OAK TREE

Filed Dec. 1, 1967

INVENTOR.

FOSTER MILLS

BY Rummler and Snow

Attys

United States Patent Office

Plant Pat. 2,899
Patented July 1, 1969

2,899
PIN OAK TREE
Foster Mills, 2001 Lithopolis Road,
Groveport, Ohio 43125
Filed Dec. 1, 1967, Ser. No. 687,404
Int. Cl. A01g 5/00
U.S. Cl. Plt.—51 1 Claim

ABSTRACT OF THE DISCLOSURE

This disclosure concerns a new and distinct variety of *Quercus palustris* (commonly known as a pin oak) characterized by its leaves which are highly variegated with ivory flecked with green and the underside being of a lighter color, and the wood on the branches having an orange to brown streaking.

*Background of invention*

This new variety of pin oak was discovered by me on my growing grounds at 2001 Lithopolis Road, Groveport, Ohio in 1957, as a seedling and has now grown to a height of ten feet. Each year since the discovery, it has consistently had the same variegation of leaves and growth habits. During the past year I have grafted some cuttings from this parent tree on regular pin oak seedlings and all the grafts came back true to form of the parent tree, and with the same variegated leaves. I now have twelve of these grafts growing in a seedling bed.

*Description of the drawing*

My new variety of pin oak is shown in the accompanying full-color drawing in which.

*Description of the new plant variety*

Figure 1:
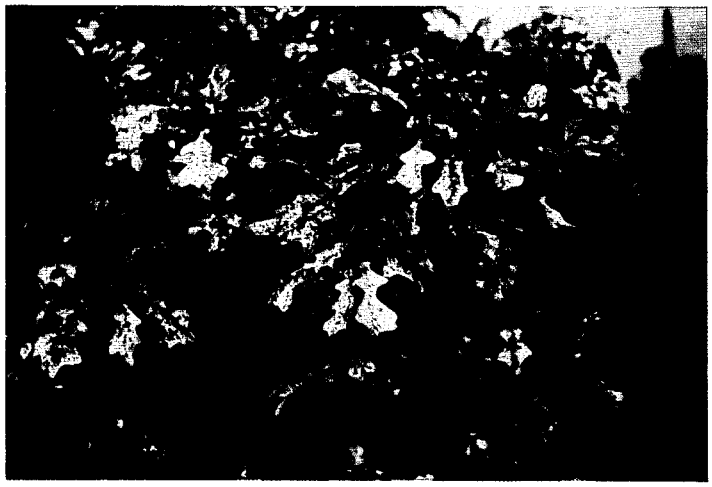
FIG. 1 is a close up view of the leaves.
Figure 2:
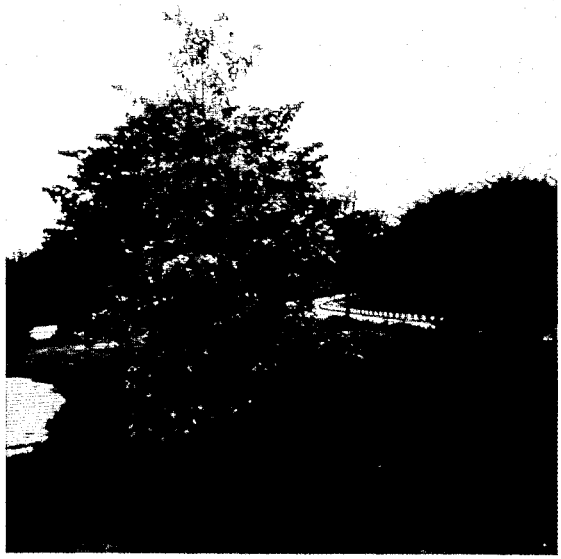
FIG. 2 is a view of my mature pin oak variety.

The following is a detailed description of my new variety of pin oak with the color designation according to a Dictionary of Color by Maerz and Paul:

Origin: Seedling.
Parentage: Unknown.
Classification: *Quercus palustris*, commonly known as a pin oak.
Form: Tree.

Shape: Symmetrical—pyramidal head.
Heighth: Present 10–12 feet.
Trunk size: 3 to 3½".
Bark: Slightly rough.
Growth rate: 10–12 inches per year.
Strength: Strong, excellent and sturdy.
Branches:
- *Angle of attachment.*—90°–100°.
- *Spacing.*—Moderately light.
- *Size:*—Typical palustris.
- *Bark.*—Smooth, orange, brown streaking.

Lenticels: Typical palustris.
Foliage:
- *Leaves.*—Moderate, typical pin oak.
- *Size.*—Length—4 to 4½". Width—2 to 2½".
- *Ribs and veins.*—Pinnate.
- *Shape.*—Oblong lanceolate.
- *Texture.*—Smooth.
- *Margin type.*—Toothed, separated by wide sinuses.
- *Pubescence distribution.*—Auxiliary tufts at vein and mid-rib junction.
- *Color.*—Upperside—highly variegated, ivory colored, approximately Plate 10, C–2 with green flecking, approximately Plate 23, L–7. Underside—light green, approximately Plate 22, H–1 less flecking, color approximately Plate 19. Petioles—⅜" to ½". Ribs and veins—light pea green.

This new variety has a very attractive appearance and is an ornamental shade tree. It has many of the same growth habits of *Quercus palustris,* with typical symmetrical pyramidal shape, and with lower branches starting to drop. Leaf shape is typical pin oak, however the leaf color is the distinguishing characteristic that makes this new variety advantageous over the common pin oak.

I claim:

1. A new and distinct variety of pin oak tree (*Quercus palustris*) substantially as shown and described, characterized particularly as to novelty by the leaves which are highly variegated with ivory flecked with green on their upper side and the under side being of a lighter ivory flecked with lighter green.

No references cited.

ROBERT E. BAGWILL, *Primary Examiner.*